United States Patent [19]

Duescher

[11] Patent Number: 4,543,718

[45] Date of Patent: Oct. 1, 1985

[54] CAST CUTTER APPARATUS

[75] Inventor: Wayne O. Duescher, St. Paul, Minn.

[73] Assignee: Twin City Surgical, Inc., St. Paul, Minn.

[21] Appl. No.: 575,817

[22] Filed: Feb. 1, 1984

[51] Int. Cl.⁴ .......................... B27B 9/00; B26B 25/00
[52] U.S. Cl. ......................................... 30/124; 30/133; 30/166 R; 310/38
[58] Field of Search ..................... 30/124, 166 R, 133, 30/272 R, 272 A; 310/38

[56] References Cited

U.S. PATENT DOCUMENTS

| | | | |
|---|---|---|---|
| 2,803,433 | 8/1957 | Smith | 310/38 X |
| 2,960,643 | 11/1960 | Boyd | |
| 3,060,334 | 10/1962 | Favre | 310/38 |
| 3,199,194 | 8/1965 | Shaheen | 30/276 |
| 3,317,916 | 5/1967 | Thompson et al. | |
| 3,425,011 | 1/1969 | Ito | 310/38 |
| 3,483,410 | 12/1969 | Siegelman et al. | |
| 3,548,225 | 12/1970 | Vit | 310/38 |
| 3,725,561 | 4/1973 | Paul | |
| 3,952,412 | 4/1976 | Rhodes | 30/166 R |
| 3,959,673 | 5/1976 | Montagu | 310/38 |
| 3,970,979 | 7/1976 | Montagu | 310/36 |
| 4,076,998 | 2/1978 | Montagu | 310/36 |
| 4,135,119 | 1/1979 | Brosens | 310/36 |
| 4,281,457 | 8/1981 | Walton | 30/124 |
| 4,421,111 | 12/1983 | Rothman | 30/124 |

Primary Examiner—Jimmy C. Peters
Attorney, Agent, or Firm—Merchant, Gould, Smith, Edell, Welter & Schmidt

[57] ABSTRACT

An oscillating tool, particularly a cast cutter (40) having a support housing (46) with a cutting blade (70) interconnected to the housing (46) proximate one end thereof for oscillatory rotational movement about an axis (56) is disclosed. A torsion shaft (54) is fixedly interconnected at a first end (102) to the housing (46) so as to prevent rotational oscillation at the first end of the torsion shaft (54). The torsion shaft (54) further has a free second end (100) enabling oscillatory rotational movement of the second end (100) generally about the axis (56) of the cast cutter blade (70). A hollow tubular rotor support member (58) substantially more rigid than the torsion shaft (54) is attached to the torsion shaft (54) proximate the second free end (100) of the torsion shaft (54). The hollow tubular rotor support member (58) is concentrically positioned about the torsion shaft (54) and extends from proximate the second end (100) of the torsion shaft (54) along a major portion of the torsion shaft (54) toward the first end (102) of the torsion shaft (54). The cutting blade (70) is interconnected to the hollow tubular rotor support member (58) and torsion shaft (54) arrangement proximate the second end (100) of the torsion shaft (54) for oscillatory rotational movement therewith. A magnetically interactive rotor (60) is fixedly attached to the hollow tubular rotor support member (58) at a location axially removed from the cutting blade (70) for oscillatory rotational movement therewith. A magnetically interactive stator (66) axially adjacent but radially removed from the rotor (60) induces rotational oscillation of the rotor (60) and consequently the tubular member (58). Accordingly a rotational oscillatory movement of the cutting blade (70) is provided.

17 Claims, 27 Drawing Figures

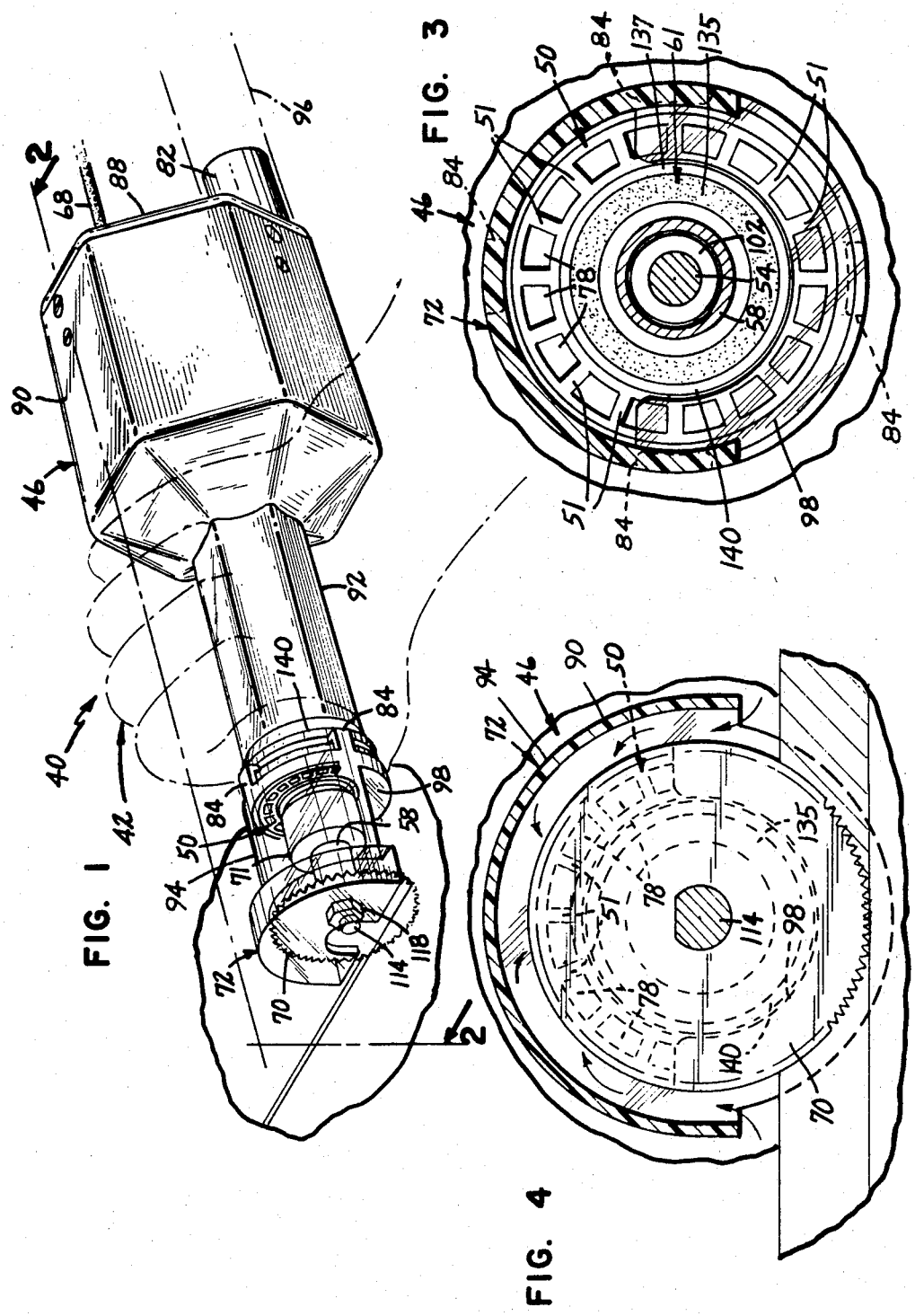

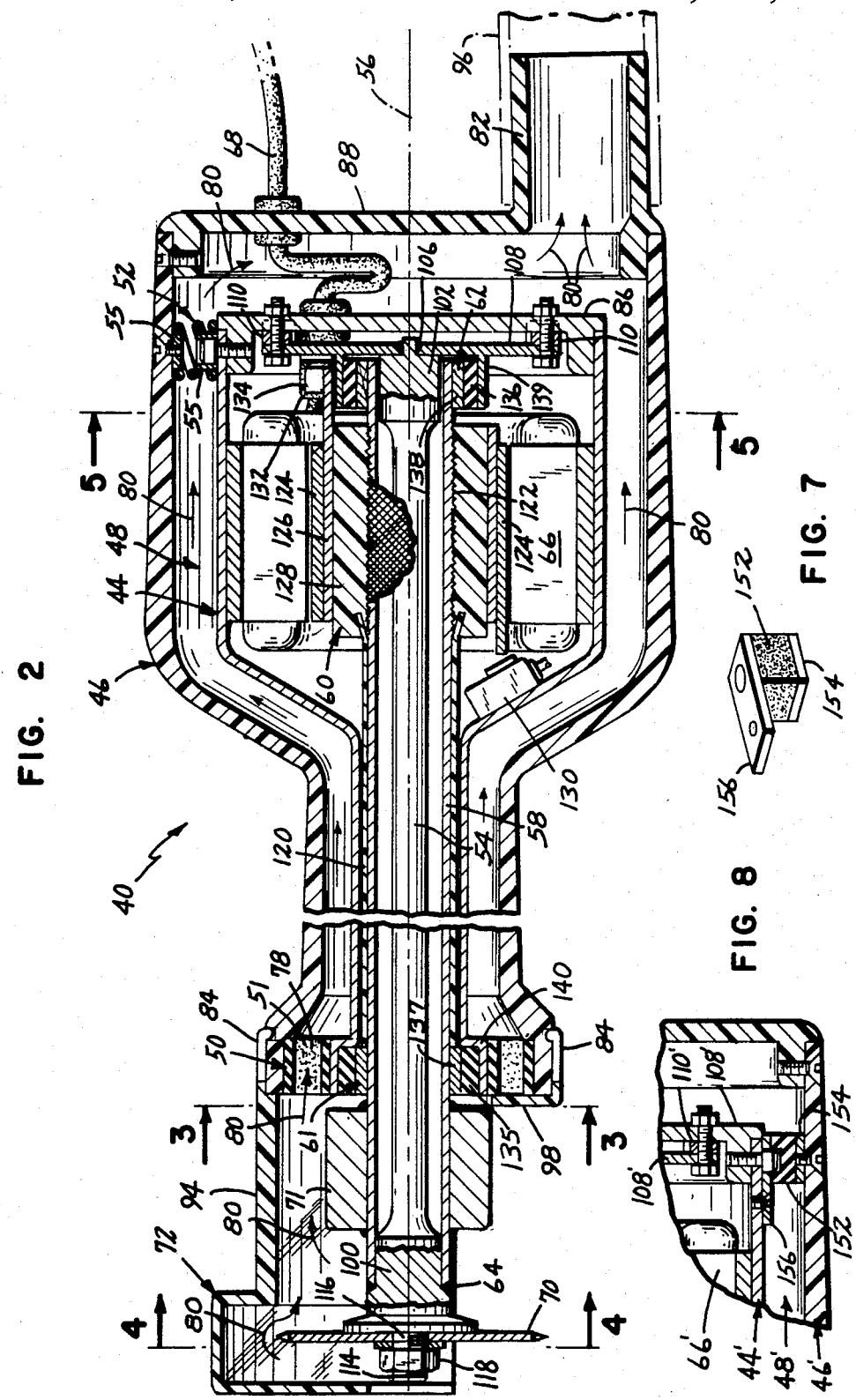

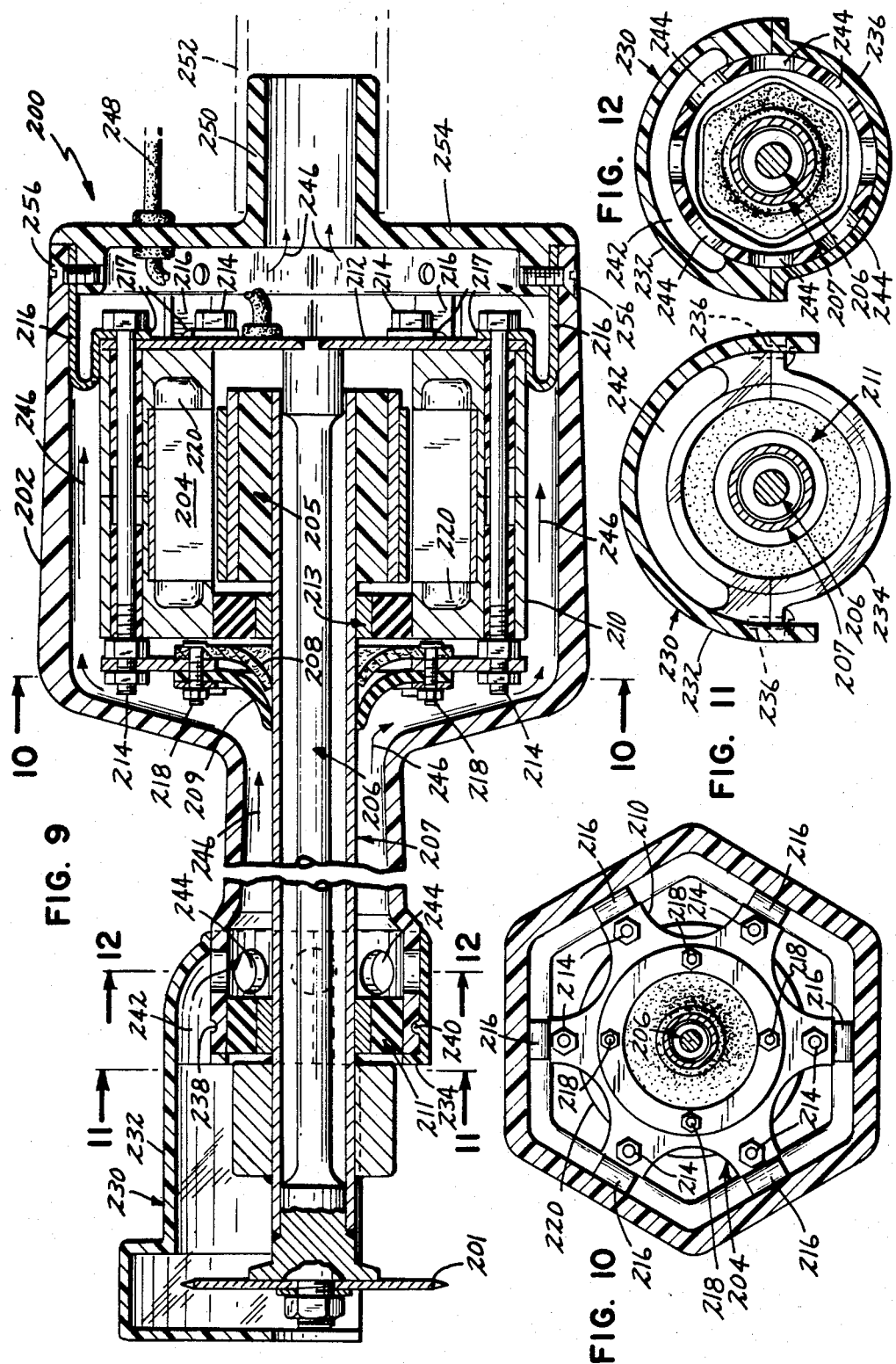

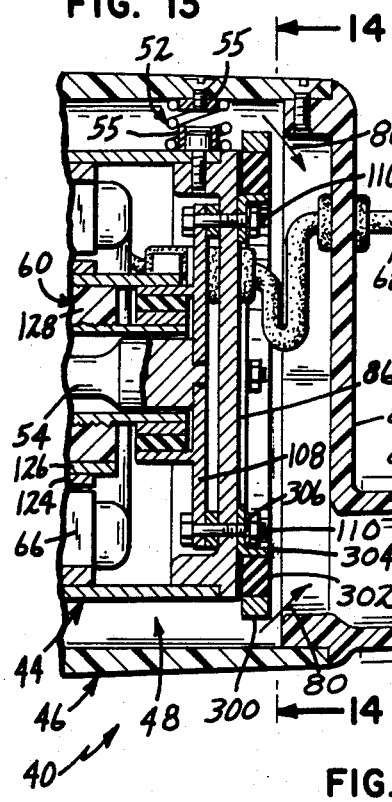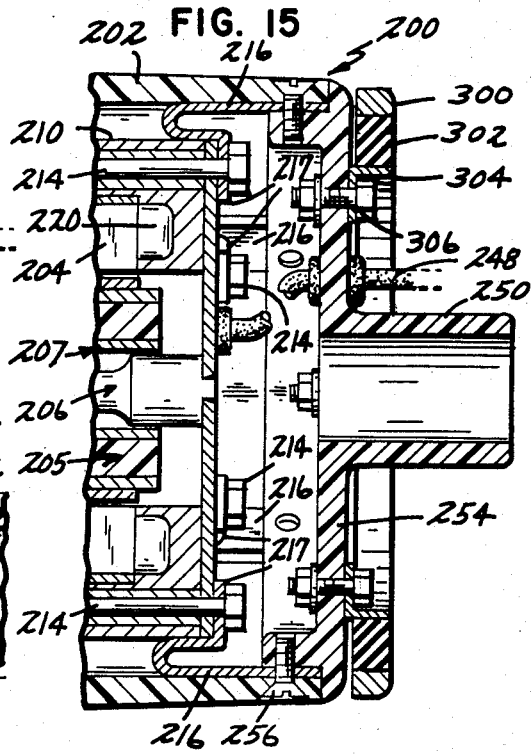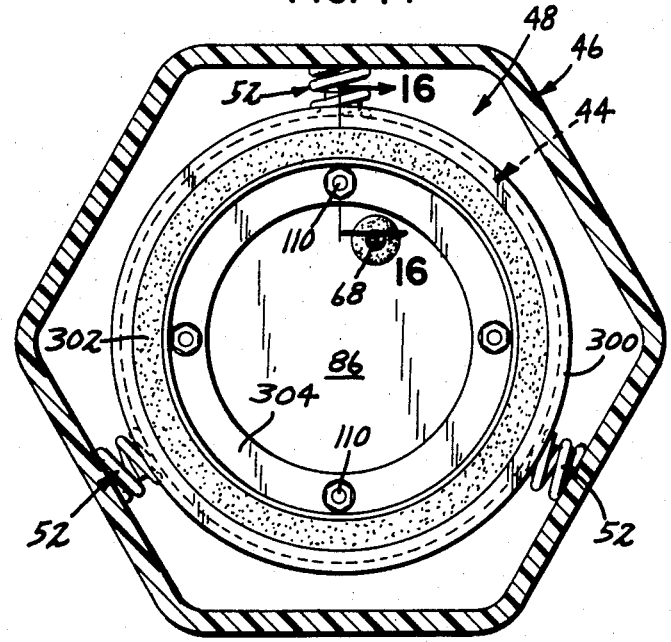

CAST CUTTER APPARATUS

BACKGROUND OF THE INVENTION

The present invention relates to an oscillatory tool utilizing an oscillatory motor in a spring/mass vibration tuned system, and more specifically, to a surgical cast cutter utilizing an oscillatory motor in a spring/mass vibration tunned system.

In the past, rotating and oscillating cast cutters have been used to cut through the plaster material of casts commonly used to immobilize an extremity or a portion of the body. Rotating cast cutters and oscillating cast cutters having a large angular displacement are dangerous, not only to the patient but also to the attendant or physician removing the cast. To alleviate the dangers involved, rotating cast cutters have been abandoned and the oscillating type of cast cutter redesigned to provide an oscillation of a limited angular displacement. However, the excursion angle or displacement angle must be large enough and the frequency high enough to provide an efficient cast cutting action.

Cast cutters providing an oscillatory cutting motion are generally bulky and extremely noisy, having been developed on the principle of conversion from a rotating motor motion to oscillatory blade motion through a variety of mechanical transducing linkages and gears. The bulkiness of prior art cutters renders them unwiedly and awkward to use. In addition, and of particular importance, the noise generated in their use is extremely annoying to the operator and frightening to the patient being worked on.

U.S. Pat. No. 3,199,194 issued to Shaheen discloses a surgical cast cutter utilizing an oscillatory motor in an attempt to do away with the mechanical linkages and gearing typically required to transduce the rotating motion of a motor into the oscillatory motion of the cutting blade. In particular, Shaheen utilizes the generation of an alternating magnetic field to provide angular oscillations to the cast cutter blade. This is accomplished by directly attaching the cast cutter blade to two rotors placed on either side of the blade and further positioning two stators on opposite sides of the blade/rotor assembly. The stators are alternately energized to cause the cast cutter blade to oscillate about its axis. Despite its many supposed advantages, the cast cutter is subject to wear due to the rapid deceleration and acceleration of the stators and the armature assembly as there is no provision for absorption or diffusion of the angular energy. Additionally, the weight of the cast cutter is largely adjacent the blade resulting in poor handling characteristics. Furthermore, the torque to inertia ratio of the system is unsatisfactorily low requiring a large amount of power to overcome the inertia of the system and provide a large enough excursion angle. Additionally, electrical current must be provided to the rotating armature necessitating the use of slip ring connectors or the like which complicates the overall design and increases the overall cost of manufacturing and maintenance.

Various embodiments of oscillating systems have been utilized for such applications as optical scanners (see U.S. Pat. Nos. 3,959,673 and 4,135,119), and galvanometers (see U.S. Pat. No. 3,317,916). However, these references do not suggest or teach a tool apparatus whose desired operating frequency is approximately that of its natural frequency. The references disclose devices oscillating a very slight mass and having a relatively soft spring which only has enough stiffness to return the mass; e.g. mirror, to a center or neutral position when the devices are not energized. The torque-to-inertia ratio of these devices is relatively high such that the devices can be operated over a broad range of frequencies. The excursion angles of these devices are relatively constant and vary slightly over a broad range of operating frequencies. Furthermore, these devices, due to the slight mass, do not provide for the storage of a large amount of kinetic energy during the oscillatory motion of the system to facilitate the energy requirements of an oscillatory tool such as a cast cutter, the power requirements of the devices disclosed by the references being slight. The primary purpose of the torsion bar arrangement in these devices is to enable variable frequency of operation and accurate positioning of the tool which is being oscillated. Further, there is no attempt to absorb or diffuse angular energy to reduce wear. For this and other reasons the references do not teach the use of a torsion bar arrangement for an oscillatory tool utilizing an oscillatory motor in a spring/mass vibration tuned system and in particular a cast cutter which utilizes such a system.

The present invention solves the above indentified problems and others associated with the prior art.

SUMMARY OF THE PRESENT INVENTION

The present invention relates to a tool apparatus for imparting oscillatory rotational movement to a work piece engaging portion. The tool apparatus includes a housing and has an oscillatory motor including a rotor assembly and stator assembly which is supported by the housing. Support means interconnects the rotor assembly to the work piece engaging portion. The rotor assembly cooperates with stator assembly to impart an oscillatory rotational movement to the support means upon interconnection to a power supply. Torsion means is fixed against rotation proximate a first end and is configured proximate a second end for oscillatory rotational movement. The support means and the torsion means cooperate with the motor and work piece engaging portion to provide a spring/mass system tuned to provide the tool apparatus with an operating frequency approximately that of its natural frequency.

More particularly, the present invention relates to a cast cutter having a support housing with a cutting blade interconnected to the housing proximate one end thereof for oscillatory rotational movement about an axis. A torsion shaft is fixedly interconnected at a first end to the housing so as to prevent rotational oscillation at the first end of the torsion shaft. The torsion shaft further has a free second end enabling oscillatory rotational movement of the second end generally about the axis of the cast cutter blade. A hollow tubular rotor support member substantially more rigid than the torsion shaft and having a larger inside diameter than the outside diameter of the torsion shaft, it attached to the torsion shaft proximate the second free end of the torsion shaft. The hollow tubular rotor support member is concentrically positioned about the torsion shaft and extends from proximate the second end of the torsion shaft along a major porton of the torsion shaft toward the first end of the torsion shaft. The cutting blade is interconnected to the hollow tubular rotor support member/torsion shaft arrangement proximate the second end of the torsion shaft for oscillatory rotational movement therewith. A magnetically interactive rotor is fixedly attached to the hollow tubular rotor support member at a location axially removed from the cutting blade for oscillatory rotation with the tubular member. A magnetically interactive stator axially adjacent but radially removed from the rotor induces rotational oscillation of the rotor and consequently the tubular member. The torsion shaft cooperates with the hollow tubular rotor support member to provide a spring/mass system which provides the cast cutter with a desired operating frequency which is approximately that of the natural frequency of the spring/mass system and with a desired oscillation or excursion angle while exhibiting a high Q or magnitude ratio.

The present invention provides a tool and particularly a cast cutter utilizing an oscillatory motor which requires no mechanical linkage or gearing to convert rotational movement of a rotating motor into an oscillatory rotational movement. Furthermore, the oscillatory motor in cooperation with the torsion shaft/hollow tubular member arrangement provides a spring/mass vibration tuned assembly which is driven by a pure sinusoidal electrical power source is provide an operating frequency which is approximately that of the natural frequency of the spring/mass system. A further significant advantage of the present invention is the reduction of noise which is addition to being annoying to the operator has a tendency to frighten the patient being worked on. This is also particularly advantageous in the veterinary field wherein loud noises frighten animals.

It will be appreciated that while the principles of the present invention are generally discussed in light of a particular application, namely a cast cutter, the principles of the present invention have application to other tool apparatus where substantial energy is required to operate on a work piece in an oscillatory rotational fashion at an operating frequency which is the natural frequency of the tool. For example, other applications might be a polishing tool or a cutting tool for other purposes than cutting a cast.

Use of the spring/mass system wherein the hollow tubular rotor support member is concentrically positioned about the torsion shaft results in a cast cutter having a small physical size and being of a desired weight wherein the cutter is light enough to easily be handled and yet sufficiently heavy to facilitate stability and control of the cast cutter.

Damping of the torsion spring/mass system is minimized to achieve a high "Q" or magnitude ratio, herein defined as the ratio of the output amplitude as compared to the input amplitude, wherein an adequate angle of oscillation is achieved to provide the cutting blade with enough oscillation angle to generate a rigid cast cutting action. The power requirements necessitated to achieve the required excursion angle are reduced due to the relatively high torque to inertia ratio of the system.

Heat removal from the cast cutter is facilitated in the preferred embodiment of the invention since the heat generated by the electrical windings of the stator is at the outer periphery of the motor enabling removal of the heat by the passage of air over the outside perimeter of the motor. In one embodiment of the present invention, a vacuum system is provided which in addition to enabling dust and particulate removal enables the substantial simultaneous removal of heat from around the motor.

In one embodiment of the present invention, the motor is enclosed within an inner liner or shell to effectively provide a sealed unit. This reduces the likelihood that any dust or particulate will contaminate the motor.

The present invention enables the excursion angle or angle of oscillation to be readily controlled by various methods; for example, using feedback coils within the motor windings or using Hall effect devices sensing the oscillation of the motor rotor and suitable control circuitry adjusting the power supply accordingly. The excursion angle may therefore be controlled to minimize injury to a person if the cutting blade should contact the person's flesh, and yet provide an effective cutting action. While the basic frequency or oscillation of the unit is fixed by the physical size of the mechanical parts of the unit, the frequency may be readily adjusted through the use of suitable sensors and control circuitry to vary the frequency input to the motor so as to tune the system.

In one embodiment of the present invention, the excursion angle is limited by use of mechanical stops thereby providing the cast cutter with an additional safety feature to assure that the oscillatory movement of the blade does not exceed a certain excursion angle.

The present invention provides for distribution of the torsion spring/mass system's mass/inertia between the motor and the blade mounting end of the spring/mass system to provide for hand balance and reduce the stress in the motor design.

In the preferred embodiment of the cast cutter, the spring/mass system is provided with a large amount of mass to enable the storage of kinetic energy to facilitate the cutting action of the blade when the cutting blade engages the cast material.

The preferred embodiment of the present invention utilizes an essentially nonsparking brushless DC motor as compared to a brush type DC or universal motors commonly used. Accordingly, the present invention may be utilized in explosive environments.

The present invention partially due to the reduced linkage requirements, etc. is relatively inexpensive to manufacture and maintain. Additionally, the present invention does not require that electrical current be supplied to a rotating armature thereby simplifying design and reducing costs. Also, the spring/mass vibration system provides for absorption and diffusion of angular energy thereby reducing wear on the oscillatory system due to the rapid changes in rotational direction.

Furthermore, the cast cutter of the present invention exhibits human factors considerations not present in other cast cutters. In addition to other features, the present invention is easy to hold and manipulate due in part to its outer configuration and mass distribution. The present invention provides a hand grip location between the cutting blade and the motor facilitating ease of use and resulting in a well balanced and stable tool.

A further advantage of the present invention is that it may be fine tuned electrically to the proper frequency and/or excursion angle. This substantially eases the tolerances which must be met during manfacture and assembly of the invention. Furthermore, the invention is provided with increased flexibility.

These and other various advantages and features of novelty which characterize the invention are pointed out with particularlty in the claims annexed hereto and forming a part hereof. However, for a better understanding of the invention, its advantages, and objects obtained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views;

FIG. 1 is a view in perspective illustrating a preferred embodiment of the present invention being held in an operational mode;

FIG. 2 is an enlarged fragmentary view in longitudinal section as seen generally along line 2—2 in FIG. 1 with portions broken away;

FIG. 3 is a view in transverse section as seen generally along line 3—3 in FIG. 2;

FIG. 4 is a view in transverse section as seen generally along line 4—4 in FIG. 2;

FIG. 7 is a perspective view of an alternative mounting structure for mounting the inner housing relative to the outer housing of the embodiment shown in FIG. 2;

FIG. 8 is a fragmentary detailed sectional view showing the mounting pad element of FIG. 7 in operational position;

FIG. 9 is a view similar to FIG. 2 showing a modified embodiment of the present invention utilizing a single housing;

FIG. 10 is a view in transverse section as seen generally along line 10—10 in FIG. 9;

FIG. 11 is a fragmentary view in transverse section as seen generally along line 11—11 in FIG. 9;

FIG. 12 is a view in transverse section as seen generally along line 12—12 in FIG. 9;

FIG. 13 is a partial sectional view of yet another embodiment of the present invention including an embodiment of a secondary spring/mass system;

FIG. 14 is a view as seen generally along line 14—14 of FIG. 13;

FIG. 15 is a partial sectional view of yet another embodiment of the present invention including an embodiment of a secondary spring/mass system mounted in a differing location than that of FIG. 13;

FIG. 16 is a sectional view as seen generally along line 16—16 in FIG. 14;

DETAILED DESCRIPTION OF THE PREFERRED EMBODIMENT

Figure 5:
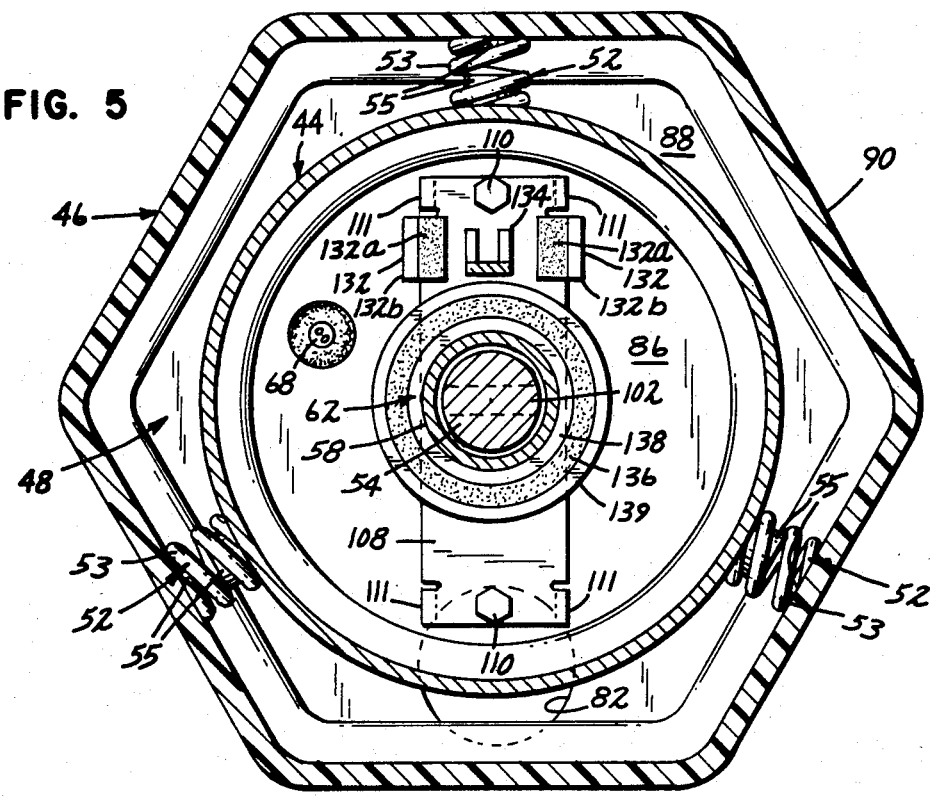
FIG. 5 is an enlarged view in transverse section as seen generally along line 5—5 in FIG. 2.

The preferred embodiment of the present invention will be hereafter described for a cast cutting application, although it will be appreciated that the principles of the present invention might be utilized in other applications.

Referring now to FIG. 1, there is shown in perspective a preferred embodiment of the cast cutter of the present invention, generally designated by the reference numeral 40, being held in an operational mode by a user's hand 42. As illustrated in FIG. 2, the preferred embodiment of the cast cutter 40 includes an inner housing 44 mounted within an outer housing 46 so as to be generally separated by a space 48. In the preferred embodiment the two housings 44, 46 are separated by about one-quarter ($\frac{1}{4}$) inch. The outer housing 46 is preferably made of a plastic material or any other suitable material while the inner housing 44 is preferably made of steel. The inner housing 44 is somewhat resiliently mounted within the outer housing 46 by suitable mounting assemblies 50 and 52 proximate the front and back ends of the inner housing 44, respectively. The mounting assemblies 50 and 52 are constructed and arranged to mechanically isolate the inner housing 44 from the outer housing 46 so as to significantly reduce or minimize noise or vibration transfer paths between the two housings. In the preferred embodiment shown, the mounting assembly 52 is a coil spring 53 suitably attached to mounts 55 on the inside wall of the outer housing 46 and the outside wall of the inner housing 44. The mounting assembly 50 as illustrated in FIGS. 3 and 4, includes a ring-like collar assembly having a plurality of circumferentially spaced apart spokes 51 extending radially outward. The mounting assembly 50 is preferably made of a rubber or plastic material which minimizes the transfer of noise or vibration between the inner and outer housings 44, 46 to which it is interconnected.

Positioned within the inner housing 44 and extending longitudinally of the housings 44, 46 beyond the front end thereof is a solid, elongated rod member 54, hereafter referred to as a torsion bar or shaft. The torsion bar 54 is fixedly secured at the back end to the inner housing 44 so as to prohibit rotation of the torsion bar 54 about its longitudinal axis 56. (In the preferred embodiment the longitudinal axis 56 of the torsion bar 54 is generally aligned with the longitudinal axis of both the inner and outer housings 44, 46).

The torsion bar 54 is welded or suitably interconnected generally at location 64 proximate its front end to a hollow, elongated tubular member 58 concentrically positioned about the torsion bar 54 and extending along a major portion of the torsion bar 54. The hollow tubular member 58 which is relatively light and stiff serves as a support member for a rotor assembly 60 mounted about the circumference of and longitudinally along a portion of the tubular member 58 proximate the back end thereof. The back end of the tubular member 58 is not fixedly attached to either of the housings 44, 46 and as such is rotatable with the rotor assembly 60 as is the second end of the torsion bar 54 which is interconnected to the hollow tubular member 58. The position of the hollow tubular member 58 relative to the housings 44, 46 and the torsion bar 54 is maintained by bearing assemblies 61 and 62 proximate the front and back ends of the hollow tubular member 58, respectively, as well as by the interconnection of the hollow tubular member 58 to the torsion bar 54 generally at the location 64. Preferably the inner housing 44 is separated from the hollow tubular member 58 along a front end portion thereof. In the preferred embodiment this separation is approximately one-sixteenth (1/16) inch.

Longitudinally adjacent and radially outwardly spaced from the rotor assembly 60 is a stator assembly 66 which is electrically interconnected via a suitable electrical lead 68 to appropriate control circuitry, hereafter discussed, which in turn might be connected to an AC power source (not shown) such as a conventional wall outlet. The stator assembly 66 is fixedly attached to the inside wall of the inner housing 44 such that upon application of suitable current, magnetic flux fields are created causing oscillatory rotation of the rotor assembly 60 and accordingly the hollow tubular member 58 as well as the front end of the torsion bar 54.

Interconnected to the front end of the torsion bar 54 for oscillatory motion therewith is a circular cutting blade 70. In the preferred embodiment, it is anticipated that a two (2) to two and one-half (2½) inch blade will be used although it will be appreciated that other sized blades may be utilized. The top half of the cutting blade 70 is preferably covered by a semicylindrical shield 72, more preferably a clear plastic shield which extends back toward the housing 46 and is interconnected to the front end of the outer housing 46 for sliding rotational movement thereabout. In the preferred embodiment shown in FIG. 2, the semicylindrical shield 72 includes extensions 84 which are adapted to slideably and removeably engage a groove 74 such that the shield 72 may be removeably snapped into place and rotatably positioned at any angle about the circumference of the cutting blade 70.

The shield 72 defines a space 76 between the shield 72 and the torsion bar 54/hollow tubular member 58, the space 76 being in communication with the space 48 separating the inner and outer housings 44, 46 through apertures 78 defined by the spaced apart spokes 51 in the ring-like mounting assembly collar 50 interconnecting the outer housing 46 to the inner housing 44. Accordingly, dust and particulate may be removed as generally indicated by the arrows 80 from the vicinity of the cutting blade 70 and exhausted through an exhaust port 82 by interconnection to a vacuum source (not shown). Futhermore, the moving air assists in cooling the motor assembly as it flows over the inner housing 44 in the vicinity of the stator assembly 66.

Also in the preferred embodiment as illustrated in FIGS. 3 and 4, the shield 72 includes a semicylindrical collar portion 98 integral with and rotatable with the shield 72, so as to enclose the apertures 78 about the bottom half of the circumference of the collar 50 such that vacuum suction is occurring only through the apertures 78 at the top half of the mounting assembly 50. This facilitates the removal of dust and other particulate during the cutting operation.

The torsion bar 54, the hollow tubular member 58, the motor assembly, and whatever additional mass is associated therewith function to provide a mechanically tuned torsion spring/mass vibration system which is driven by a pure sinusoidal electrical power source to operate at a frequency which is the natural frequency of the system and which may be electrically fine tuned by suitable control circuitry. Damping of the system is minimized to achieve a high "Q" or magnitude ratio to provide the cutting blade 70 with sufficient oscillation or excursion angle to generate a rigid cast cutting action such as is required of cast cutters. In this spring/mass system, the torsion bar 54 provides the spring action while the hollow rigid tubular rotor supply member 58 is much more resistant to being twisted about its longitudinal axis than the torsion bar 54, having preferably less than one-tenth (1/10) the spring compliance or characteristics of the torsion bar 54. In the preferred embodiment shown the torsion bar 54 is made from a stainless steel material and has a diameter of approximately five-sixteenths (5/16) inch and a length of approximately ten (10) inches. The diameter of the torsion bar 54 is kept small so that it does not contribute substantially to the overall inertia of the system. The hollow tubular member 58 is similarly constricted of a stainless steel material and has an outside diameter of approximately five-eighths (⅝) to three-fourths (¾) inch with a length only sighly less than that of the torsion bar 54. Additional mass generally designated by the reference numeral 71, is preferably fixedly interconnected to the hollow tubular member 58 proximate the front end thereof for rotation therewith, so that the overall longitudinal weight distribution of the cast cutter is such that approximately 75 percent of the overall weight is positioned proximate the back end of the spring/mass system in the motor housing and 25 percent of the mass is positioned at the front end of the spring/mass system with the overall weight of the cast cutter being approximately two and one-quarter (2¼) to three and one-half (3½) pounds, the rotor assembly 60 or armature having a weight of approximately one-half (½) to three-quarters (¾) pound. Furthermore, the mass 71 assists in absorbing angular energy so as to minimize the continuous jarring impact on the system due to the oscillatory back and forth movement.

The operating or natural frequency (wN) of the spring/mass system can be mechanically tuned to the desired operating frequency by varying the mass (M) or the spring constant (K) of the system according to the following equation:

$$wN = \sqrt{\frac{K}{M}}$$

As illustrated in FIGS. 1 and 2, the outer configuration of the cast cutter 40 defines 3 major areas; the motor housing portion 90 housing the rotor and stator assemblies, a hand grip portion 92, and a blade end portion 94 which includes and is shielded by the shield 72. The cast cutter has an overall length of approximately eleven (11) inches. As illustrated, the motor housing portion 90 is of significantly greater transverse cross section than the hand grip portion 92 and the blade end portion 94. The motor housing portion 90 has an outside diameter of approximately three (3) inches while the hand grip portion 92 has an outside diameter of approximately one and five-eights (1⅝) inches.

The overall configuration of the cast cutter 40 exhibits substantial human factors considerations. The plastic shield 72 significantly enhances the safety of the cast cutter 40. Furthermore, the rotatable plastic shield enables the cast cutter blade to be utilized at all angles of orientation about its longitudinal axis. The motor housing portion 90 is configured so as to provide a relatively flat resting surface such that when placed on a flat surface such as a table the cast cutter will remain stationary. The exhaust port 82 is preferably positioned such that when the cast cutter is placed on a table, the conduit 96 interconnected to the exhaust port 82, will be resting on the table. Also, the overall weight distribution of the cast cutter 40 is preferably such that when placed on a relatively flat surface, the cast cutter will rest on the motor housing portion 90 with the blade 70 elevated above the surface of the table. This will minimize possible injury and damage caused by an oscillating blade when the unit is placed on a table or by the unit resting on the blade 70 at the front end thereof. In addition, the outer surface of the motor housing portion 90 may be inclined generally radially inwardly in a direction toward the back end at an angle of approximately five (5) degrees to further facilitate raising the blade 70 above the surface of the table. Further, the back walls 86, 88 are removably attached to the remainder of the inner and outer housings 44, 46, respectively, to facilitate access to the working parts of the cast cutter.

The overall symmetry of the cast cutter unit and in particular the hand grip portion 92 enables the cast cutter 40 of the present invention to be utilized at all angles of orientation. The hand grip portion 92 of the preferred embodiment has a hexagonal shape which provides for better hand control and blade orientation than a round shaft, the hexagonal configuration being a trade-off between a round configuration and a square configuration. The hand grip portion 92 has an outside diameter and longitudinal length which will adapt to fit a user's hand comfortably. Preferably, the hand grip portion 92 will fit 95 percent of potential user's hands and more preferably have an outside diameter of approximately one and five-eighths (1⅝) inches and a longitudinal extent of approximately four (4) inches. Also, preferably the hand grip portion 92 will be tapered radially outwardly in a direction toward the front end thereof as this facilitates a better grip than a constant diameter hand grip portion. It will be appreciated that an alternate embodiment of the present invention might utilize a hand grip with a constant diameter or with a taper in the opposite direction. The overall oscillatory weight of the cast cutter also assists in stabilizing the cast cutter during use.

The above described cast cutter of the present invention thus provides in addition to many other features an oscillatory cast cutter with significantly reduced noise levels along with ease and safety of operation. Additional details of the preferred embodiment and alternate embodiments of the present invention will now be addressed.

As illustrated in FIG. 2, the preferred embodiment of the torsion bar 54 is enlarged at end portions 100, 102 so as to strengthen the torsion bar 54 and facilitate energy absorption and distribution. The end portions 100, 102 are interconnected to the torsion bar 54 by radius portions 101, 103 respectively, which facilitate in relieving stress between the remainder of the torsion bar 54 and its end portions 100, 102. As further illustrated in FIG. 2, the end portion 102 has a lesser outside diameter than the inside diameter of the hollow tubular member 58 such that the hollow tubular member 58 is able to rotate while the end portion 102 of the torsion bar 54 remains stationary. The end portion 100 has a portion thereof which is generally the same diameter as or slightly less than the hollow tubular member 58 to provide support therefor. The end portion 100 is further tapered outwardly toward the front end thereof to provide a large abutting support surface adjacent the cutting blade 70.

The cutting blade 70 is mounted on an axle portion 114 which is threaded along a portion 116 thereof to enable the cutting blade 70 to be removably attached by a nut and washer assembly 118. As further illustrated in FIG. 1, the plastic shield 72 is cut away to avoid any contact with the blade mounting assembly. It will be appreciated that other methods in keeping within the principles of the present invention might be utilized to mount the cutting blade 70.

The end portion 102 of the torsion bar 54 is welded at 106 to a rectangular support plate 108 extending transversely of the torsion bar 54. The support plate 108 is supported by mounting assemblies 110 and suitable stand offs 111 at a location forward of the back wall 86 of the inner housing 44. The mounting assemblies 110 might include a nut and bolt arrangement utilizing a rubber spacer. The support plate 108 enables slight axial movement of the torsion bar 54 to compensate for the slight amount of variation in torsion bar length which occurs during the oscillatory rotational movement.

The outer circumference of the hollow tubular member 58 generally between the rotor assembly 60 and the front end of the inner housing 44 is covered by an insulation layer 120 such as a shrink tube or the like. The area 122 of the hollow tubular member 58 interconnected to the rotor assembly 60 is roughened or provided with a coarse knurl about its outer circumference to facilitate adhesively affixing or otherwise attaching the rotor assembly 60 to the hollow tubular member 58.

The rotor assembly 60 in the preferred embodiment includes a plurality of alternating polarity permanent magnets 124 mounted on a steel substrate 126, the steel substrate 126 providing additional mass to the system. In the preferred embodiment, Samarium cobalt magnets are utilized to provide low mass and high magnetic strength. The magnets 124 are each curved and arranged in a circle about the hollow tubular member 58. In the preferred embodiment, the magnets 124 have a thickness of about one-eighth (⅛) inch. The magnets 124 are radially removed from and attached to a roughened surface of the hollow tubular member by an epoxy substrate 128. Positioning of the permanent magnets 124 radially outwardly of the hollow tubular member 58 further increases the torque to inertia ratio.

The stator assembly 66 which is spaced from and positioned radially outwardly of the rotor assembly 60 might be a conventionally wound stator assembly. The stator assembly 66 is attached to the inside wall of the inner housing to facilitate removal of heat by the passage of air in the space between the inner and outer housings 44, 46. The rotor stator assemblies 60, 66 cooperate to provide a one-half (½) horsepower motor. It has been found; for example, that a Clifton D-B3000, brushless DC motor rewound to take a higher voltage for use with an AC outlet, can be utilized.

It will be appreciated that in alternate embodiments the stator assembly might utilize a permanent magnet and the rotor an electromagnet. However while this might reduce the size and weight of the cast cutter, the mass most likely will be shifted and electrical interconnection to a moving stator required.

As previously indicated, the cast cutter 40 includes suitable sensing apparatus for sensing oscillation of the rotor assembly to facilitate adjustable control of the oscillation angle, which in the preferred embodiment is approximately plus and minus two and one-half (2½) degrees or five (5) degrees total, and/or to facilitate fine tuning of the frequency, which in the preferred embodiment is approximately 200 to 300 cycles per second and more preferably 220 cycles per second. For example, for certain applications the excursion angle might be adjusted to a value substantially less than five (5) degrees total. In the preferred embodiment, a Hall effect sensor device 130 is affixed to the inside wall of the inner housing 44 generally in front of the stator assembly 66 as illustrated in FIG. 2.

As illustrated in FIGS. 2 and 5, the preferred embodiment includes mechanical stops 132 which cooperate with a projection 134 from the rotating armature assembly so as to limit the amount of excursion angle. In the embodiment shown, the stops 132 are formed by rubber 132(a) vulcanized onto metal tabs 132(b) which are integral with the support plate 108 and are folded or bent into position. It will be appreciated that alternate approaches might be utilized to limit the excursion angle. For example, two circumferentially spaced apart projections from the rotating armature assembly might interact with a single projection from the support plate 108.

The bearing assemblies 61, 62 enabling oscillatory rotational movement of the hollow tubular member 58, include rubber pad elements 135, 136 respectively for minimizing vibration and noise transmission and suitable bearings 137, 138 respectively, such as an oiled brass or plastic bearing. The bearing assembly 62 is held in position by a cylindrical structure 139 while the bearing assembly 61 is held in place by being fixedly secured to a structure 140 at the front end of the inner housing 44. Although not shown, a steel sleeve might be positioned between the rubber pad elements 135, 136 and the member 58 to reduce wear. The sleeve might be a separate precision ground, hardened and polished ring adhesively attached to the nonprecision armature support member 58. This sleeve would most likely only be used with bronze or plastic bearings as an inexpensive way of having a precision surface and mechanical fit for the sliding rotational motion between the oscillating member 58 and the stationary bearing structure. It will however be appreciated that other suitable bearing structures might be utilized to rotationally support the hollow tubular member 58. For example, the bearing assembly 62 might interconnect the rotor assembly 60 to the torsion bar 54.

Figure 6:
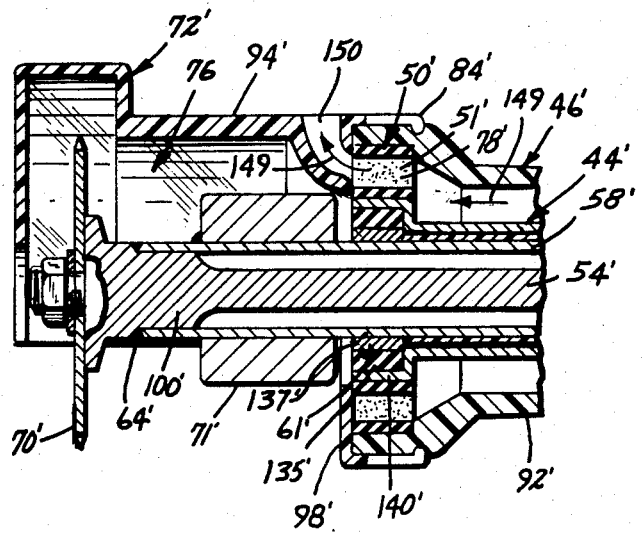
FIG. 6 is a fragmentary detailed sectional view showing a modified portion of FIG. 2.

Illustrated in FIG. 6 is an alternate embodiment of the present invention, wherein the motor assembly is cooled by forcing air between the inner and outer housings 44', 46' as generally indicated by the arrows 149 generally from the back end to the front end by a source of pressurized air (not shown). The air exits through an exit port 150 defined by a modified plastic shield 72' adjacent the collar portion 98'.

Illustrated in FIGS. 7 and 8, is one possible alternate embodiment of the inner housing 44 mounting assembly 52. In this embodiment, the mounting assembly includes a rubber pad 152 vulcanized or otherwise suitably attached to a piece of metal 154 and 156 on opposite sides thereof. The combination is then suitably secured to the inner and outer housings 44', 46' as generally illustrated in FIG. 8.

Illustrated in FIGS. 9 through 12 is an alternate embodiment 200 of the cast cutter of the present invention. In this embodiment a single housing 202 is utilized. The motor assembly includes a stator assembly 204 and a rotor assembly 205 somewhat similar to that of the previous embodiment. A torsion bar 206 and a hollow tubular member 207 not unlike that of the previous embodiment are also utilized to interconnect the motor assembly to a cutting blade 201 so as to provide a spring/mass system. The hollow tubular member 207 is rotatably supported by suitable bearing assemblies 211, 213 not unlike that of the previous embodiment. The motor assembly of this embodiment is effectively sealed from dust and particulate by the use of a cylindrical self oiling apparatus such as a cylindrical felt oiler 208 which is positioned in front of the motor assembly generally about the hollow tubular member 207 for lubrication of the motor armature. Positioned in front of the felt oiler 208 is a cylindrical flexible filter 209 made of a rubber or neoprene material which protects the felt oiler 208 and prevents the entry of dust or other particulate into the interior of the motor assembly. The stator assembly 204 includes a support structure 210 which is suitably attached to a support platform 212 by nut and bolt assemblies 214. The support platform 212 is in turn supported by resilient metal U-shaped mounts 216 attached to the housing 202 and including a tab portion 217 for attachment to the nut and bolt assemblies 214. The U-shaped supports 216 enable limited axial movement of the torsion bar 206 which is fixedly attached to the support platform 212 by a weld attachment or the like. The cylindrical flexible filter 209 which is attached to the support structure 210 by nut and bolt assemblies 218 has a lesser diameter than the stator assembly 204, thereby allowing air to flow between windings 220 of the stator assembly 204 and the housing 202 as generally indicated by the arrows 246.

This embodiment also includes a plastic shield 230 which includes first and second semicylindrical portions 232, 234 drawn together by threaded screws 236 for rotatable attachment onto the front end of the housing 202. The housing 202 defines a groove 238 for cooperative receipt of a ridge or tongue portion 240 of the shield 230 so as to prevent axial displacement of the shield 230. The second portion 234 is a solid collar portion while the first portion 232 defines an aperture 242 for the passage of air therethrough. Defined in the housing 202 are a plurality of apertures 244 enabling air to flow therethrough and between the housing 202 and the tubular member 207 as generally illustrated by the arrows 246. As with the previous embodiment, this embodiment includes an electrical connection 248 to the stator assembly for control by appropriate control circuitry and interconnection to a conventional AC power source. In addition, embodiment 200 includes an exhaust port 250 for interconnection via a suitable conduit 252 to a vacuum source (not shown) for creating the air flow over the stator assembly windings. As with the prior embodiments, a back wall 254 of the housing 202 may be removably attached to the remainder of the housing 202 by threaded screws 256 or the like.

As shown in FIGS. 13-19, a secondary spring/mass system having approximately 5% to 10% of the cast cutter weight and having a mechanical natural frequency tuned to approximately the same natural frequency as that of the cast cutter, might be mechanically connected to the cast cutter to further eliminate vibration. The oscillatory movement of the secondary spring/mass system is excited mechanically by the very small excursion angle of the cast cutter motor/armature structure. Upon being excited, the secondary spring-/mass system will have a defined tendency to oscillate mechanically at 180 degrees out of phase with the primary cast cutter structure and with a resultant dynamic force equal to that generated by the primary cast cutter excitation. The net result is the balance of mechanical forces and also a reduction or elimination of excursion of the cast cutter housing and thus elimination of the vibration sensation felt by the user's hand when holding the cast cutter. Such a secondary spring/mass system will have its own damping controlled by its construction materials and configuration. A number of mechanical design configurations might be employed. One configuration; as illustrated in FIGS. 13 and 14, is the use of a simple steel ring 300 adhesively bonded to an annular piece of elastomeric or rubber material 302 which in turn is attached to the back end of the cast cutter internal structure by the mounting assemblies 110 interconnected to an inner annular flange 304 having apertures 306 therein. In the embodiment shown, the steel ring 300 has a radial thickness of approximately three sixteenths (3/16) inch and a longitudinal thickness of approximately one quarter (¼) inch. The annular rubber piece 302 has a radial and longitudinal thickness of approximately three eighths (⅜) inch while the steel flange 304 has a very slight thickness. As illustrated in FIG. 15, the secondary spring/mass system or spring-/mass damper might also be attached to the outside of the plastic housing to provide for hand vibration isolation.

Figure 17:
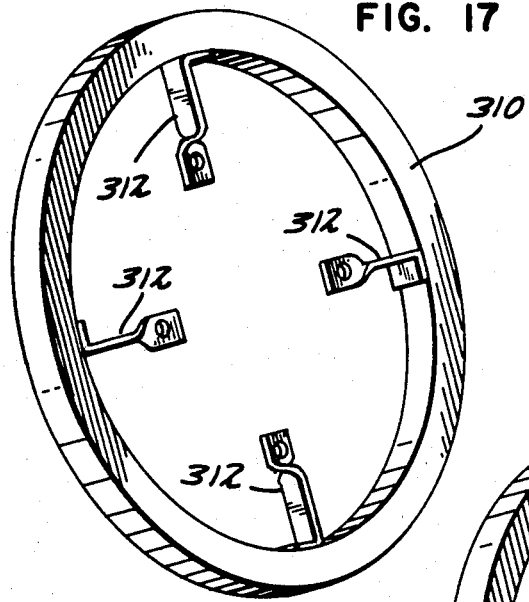
FIG. 17 is a perspective view of an embodiment of a secondary spring/mass system of the present invention.
Figure 19:
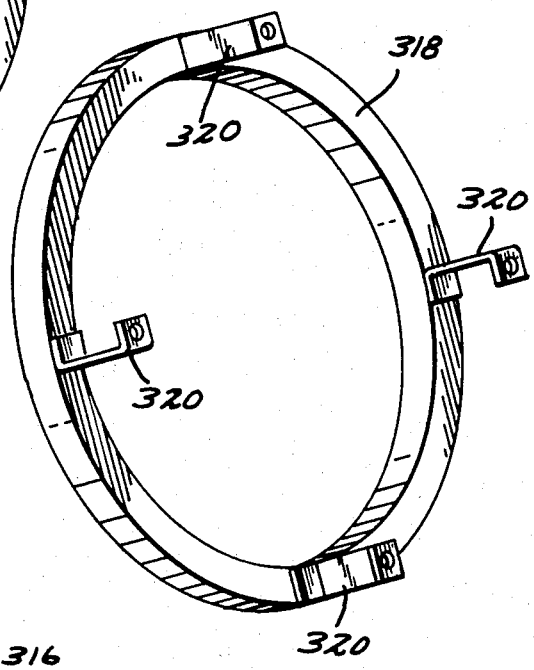
FIG. 19 is still another embodiment of a secondary spring/mass system of the present invention.
Figure 18:
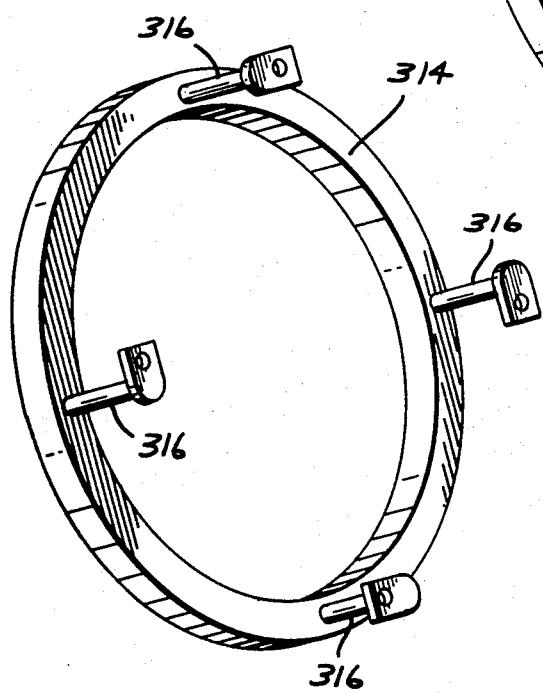
FIG. 18 is a perspective view of yet another embodiment of a secondary spring/mass system of the present invention.
Figure 20:
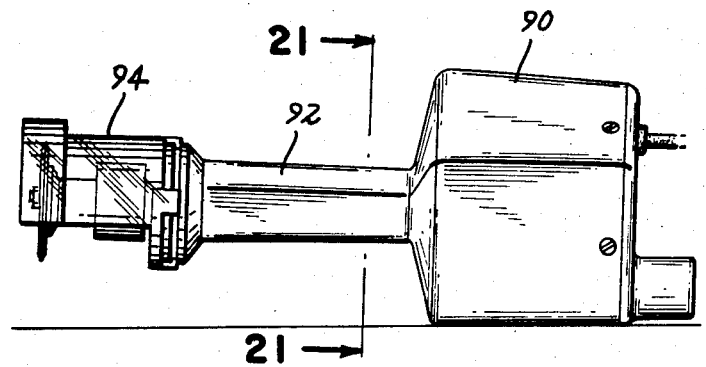
FIG. 20 is a view in side elevation of a modified housing structure.
Figure 21:
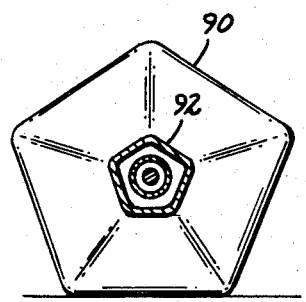
FIG. 21 is a view in transverse section generally along line 21—21 in FIG. 20.

It will be appreciated, that the secondary spring/mass system might have alternate configurations, some examples of which are illustrated in FIGS. 17 through 19. As illustrated in FIG. 17, a suitable ring structure 310 might be interconnected to the cast cutter structure by twisted, flat steel torsion springs 312. In FIG. 18, a suitable ring structure 314 is interconnected to the cast cutter structure by cantilevered rod springs 316. In FIG. 19, a suitable ring structure 318 might be interconnected to the cast cutter structure by flat springs 320.

Figure 22:
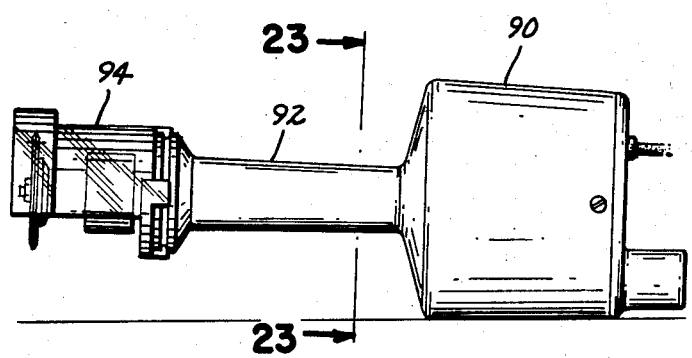
FIG. 22 is a view in side elevation of a further modified housing structure.
Figure 23:
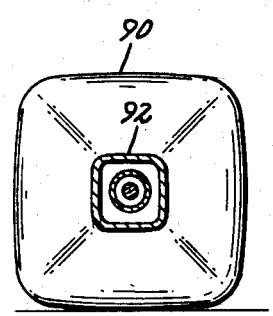
FIG. 23 is a view in transverse section as generally seen along line 23—23 in FIG. 22.

Illustrated in FIGS. 20 through 25 are alternate embodiments of the present invention having other than a housing with a hexagonal transverse cross section. In the embodiment shown in FIGS. 20 through 21, the motor housing portion 90 and the hand grip portion 92 have a pentagonal cross sectional configuration. In FIGS. 22 through 23 the motor housing portion 90 and the hand grip portion 92 have a generally square shape. In the embodiments shown in FIGS. 20 through 23, the resting surface of the motor housing portion 90 is inclined at an angle of approximately five (5) degrees such that the blade end portion 94 is farther removed from the surface on which the cast cutter is resting. In addition, the hand grip portion 92 is tapered so as to have an increasingly larger diameter toward the front or blade end of the cast cutter.

Figure 24:
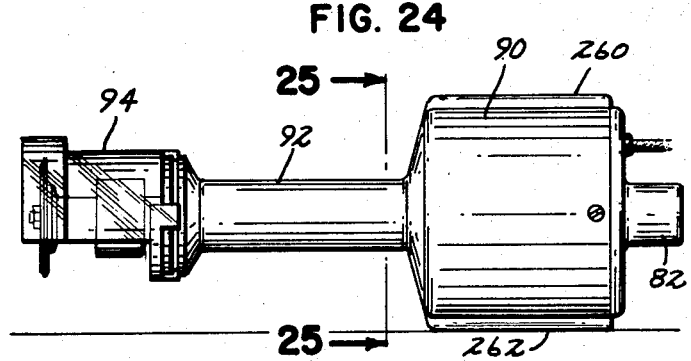
FIG. 24 is a view in side elevation of a still further modified housing structure.
Figure 25:
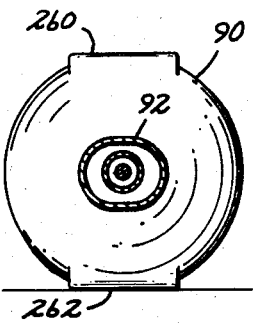
FIG. 25 is a view in transverse section as seen generally along line 25—25 in FIG. 24.

In FIGS. 24 through 25 the motor housing portion 90 has a generally cylindrical cross sectional configuration with relatively flat top and bottom surfaces 260, 262 respectively. The hand grip portion 92 has a generally oval cross sectional configuration. The exhaust port 82 is positioned proximate the center of the motor housing portion 90 in the embodiment shown in FIGS. 24 and 25 while in the embodiment shown in FIGS. 20 through 23, the exhaust port 82 is positioned adjacent the resting surface. Furthermore, the motor housing portion 90 and hand grip portion 92 of the embodiment shown in FIGS. 24 and 25 are not tapered.

Figure 26:
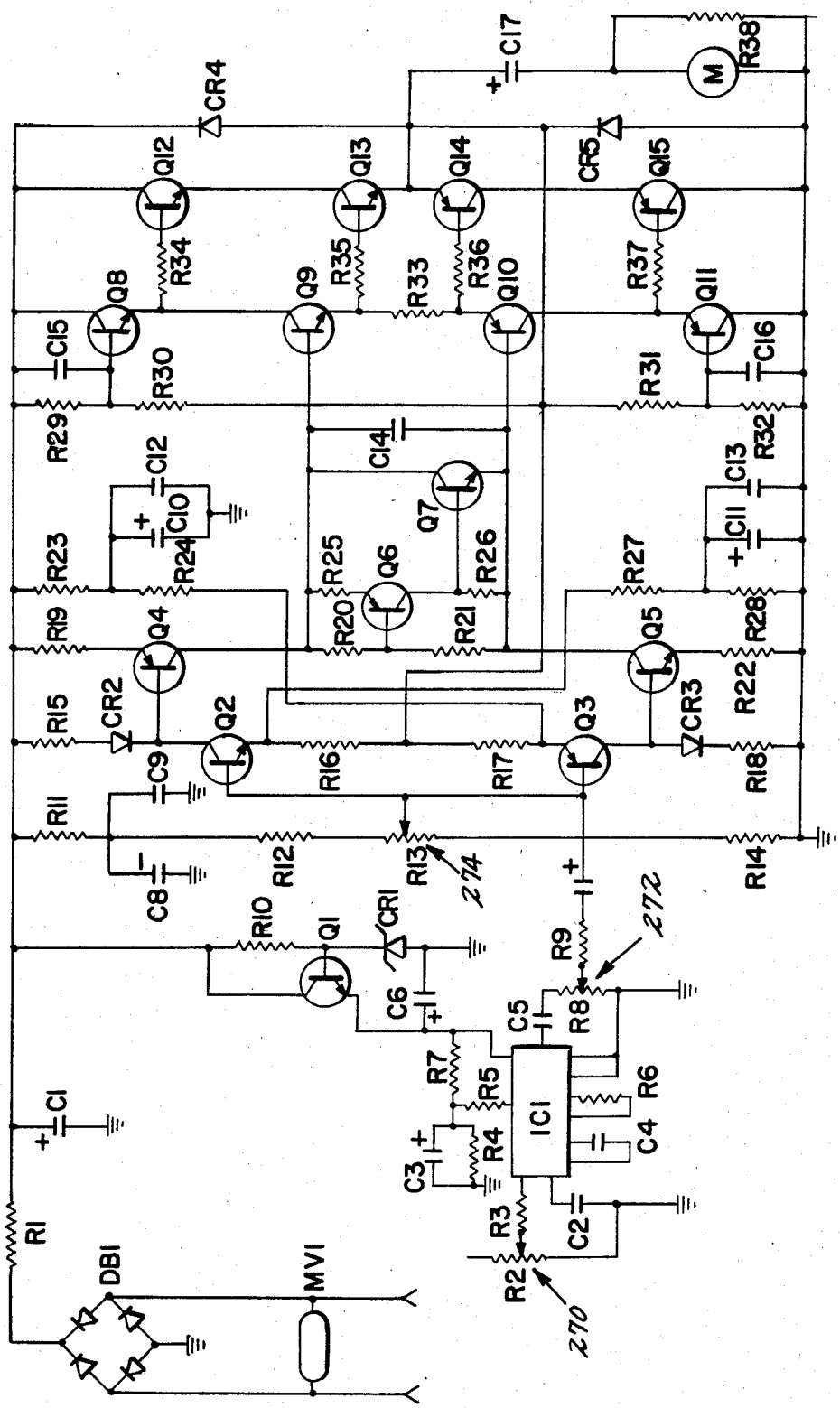
FIG. 26 is a view in schematic of an embodiment of the electrical control circuitry of the present invention.
Figure 27:
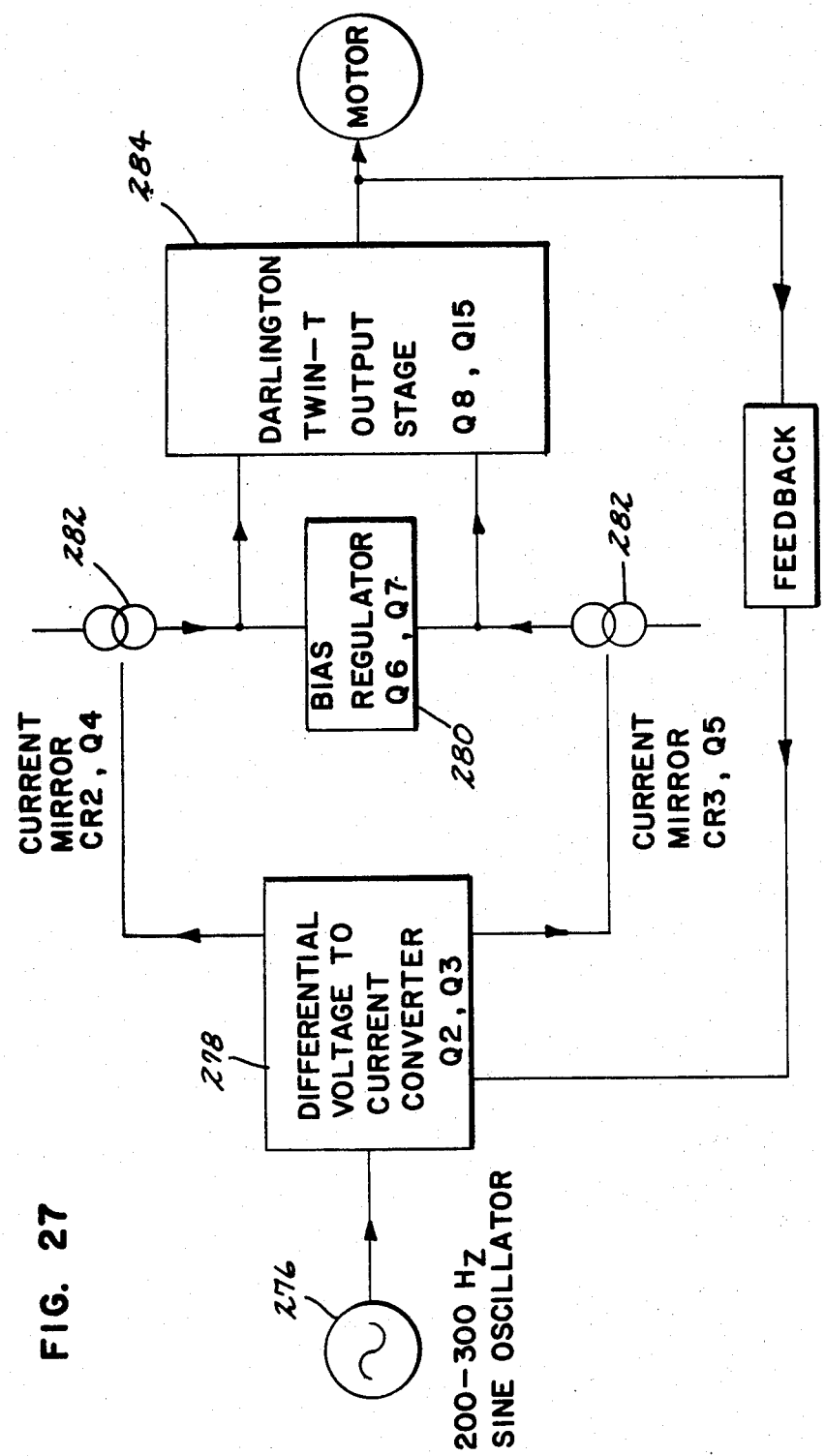
FIG. 27 is a simplified block diagram illustration of the schematic shown in FIG. 26.

Illustrated in FIGS. 26 and 27 is a schematic of control circuitry which might be utilized keeping within the principles of the present invention. The circuitry serves both as a waveform generator and as an amplifier enabling the cast cutter to be plugged into a conventional 110 volt AC outlet. As illustrated, the circuitry provides for both frequency adjustment at 270, gain control at 272, and circuit balancing at 274. The amplifier circuitry is basically a high voltage class AB audio power amplifier, incorporating active pull up and pull down. An unusual feature is the lack of an isolation transformer. This has the benefit of significant cost savings in addition to reducing the weight of the unit. The tradeoff employed is that the unit must be properly electrically isolated from the operator for safety considerations. This is similar to requirements of a modern electric drill. Furthermore, the lack of a transformer suggests a topology built around a single 170 volt supply rather than a more traditional bipolar supply. As illustrated in FIG. 27, IC1 is a waveform generator integrated circuit used to create a 200-300 Hz sine oscillator 276. It is powered via a voltage regulator Q1, CR1. Q2 and Q3 form a differential voltage to current converter 278 referred to each respective supply rail (+ and Ground). Current mirrors 282 are formed by CR2 and Q4 on the positive supply side and CR3 and Q5 on the ground side. Q6 and Q7 provide a bias regulator 280 to slightly bias a darlington output stage 284. In addition, Q6 is mounted on one of the output transistors to thermal track these transistors so that constant bias current is assured. The dual darlington output stage 284 is configured in a twin T to improve slewing in the amplifier. Each darlington stage is comprised of four transistors wired in a series configuration to handle the necessary voltage swing (approximately 170 volts peak) R29-R30 and R31-R32, each dividing this swing in half so that each output transistor need operate only half the amplifier maximum output voltage. CR4 and CR5 are used to reduce back EMF from the motor. Negative feedback is accomplished through R16 and R17 to stabilize the operating gain of the amplifier. Also a coupling capacitor C17 is used to pass the AC signal but block any DC signal.

It will be appreciated that while the amplifier control circuitry shown is specially designed to eliminate the need for power transformers which reduces weight and cost of the unit, a conventional audio/power amplifier might be utilized or the amplifier circuitry might be implemented in several different ways.

It is to be understood, however, that even though numerous characteristics and advantages of the invention have been set forth in the foregoing description, together with details of the structure and function of the invention, the disclosure is illustrative only and changes may be made in detail, especially in the matters of shape, size and arrangement of parts within the principles of the invention, to the full extent indicated by the broad general meaning of the terms in which the appended claims are expressed.

What is claimed is:

1. A cast cutter, comprising:
 (a) a support housing having first and second ends;
 (b) an elongated torsion bar, having first and second ends, fixedly interconnected at said first end to said housing so as to prevent oscillatory rotation about a longitudinal axis of said torsion bar at said first end;

(c) a hollow tubular support member, having first and second ends and being inherently more resistant to twisting movement than said torsion bar, fixedly interconnected proximate said second end to said torsion bar proximate said second end of said torsion bar, said hollow tubular support member being concentrically positioned about said torsion bar and extending axially toward said first end of said torsion bar along a portion thereof, said hollow tubular rotor support member being rotatably mounted in said housing by suitable bearing means;

(d) a magnetically interactive rotor fixedly interconnected to the said tubular member at a location axially displaced from said second end of said first tubular member for oscillatory rotational movement with said tubular member;

(e) a magnetically interactive stator positioned longitudinally adjacent and radially outwardly of said rotor, said stator cooperating with said rotor for inducing oscillatory rotational movement of said hollow tubular member upon interconnection to a suitable power source; and (f) a cutting blade interconnected to said rotor by said tubular member, said torsion bar cooperating with said hollow tubular member to provide oscillatory rotational movement of said cutting blade.

2. A cast cutter in accordance with claim 1, wherein said cast cutter further includes mechanical stops cooperating with said hollow tubular member for limiting the rotational movement of said cutting blade.

3. A cast cutter in accordance with claim 1, wherein said support housing includes an inner housing and an outer housing spaced from one another so as to define an exhaust pathway extending from approximate said cutting blade to an exhaust port leading from said outer housing proximate said first end thereof, said exhaust port being adapted for interconnection to a vacuum source whereby particulate can be drawn away from the proximity of the cutting blade.

4. A cast cutter in accordance with claim 1, wherein the angular oscillation of said cutting blade has a total angular displacement of approximately five (5) degrees.

5. A cast cutter in accordance with claim 1, wherein oscillatory frequency of 200 to 300 cycles per second is provided to said cutting blade.

6. A cast cutter in accordance with claim 1, wherein said torsion bar is interconnected to said housing proximate said first end of said housing by a support member extending transversely of the torsion bar and providing for limited axial movement of said torsion bar.

7. A cast cutter in accordance with claim 3, wherein said inner housing is supported within said outer housing by a resilient mounting assembly mechanically isolating the inner housing from the outer housing so as to minimize the transfer of noise and vibration from the inner housing to the outer housing.

8. A cast cutter in accordance with claim 1, further including a secondary spring/mass means operatively interconnected to said support housing for minimizing vibration of said support housing.

9. A cast cutter, comprising:
(a) a housing having a front end and a back end;
(b) a cutting blade proximate said front end of said housing mounted for oscillatory rotational movement about an axis extending generally longitudinally of the housing;
(c) a stator and rotor assembly displaced axially of said cutting blade, a rotor of said stator and stator assembly interconnected to said cutting blade by a hollow tubular member having front and back ends, said rotor being fixedly interconnected to said hollow tubular member for oscillatory rotational movement therewith, said rotor cooperating with a stator of said stator and rotor assembly to cause oscillatory rotational movement of said hollow tubular member and correspondingly said cutting blade upon interconnection to a suitable power source;

(d) said hollow tubular member being concentrically positioned about an elongated torsion member, having front and back ends, fixedly interconnected proximate said front end to said hollow tubular member proximate said front end of said hollow tubular member for oscillatory rotational movement therewith and rigidly fixed against rotation at said back end, said elongated torsion member being more resilient than said hollow tubular member; and (e) said hollow tubular member and said torsion member cooperating to provide a torsion spring/mass system, having a front end and a back end, whose natural frequency is approximately that of the required cast cutter operating frequency, wherein damping is minimized to achieve a high "Q" so an adequate angle of oscillation is achieved to generate a rigid cast cutting action.

10. A cast cutter in accordance with claim 9, wherein said stator generates an alternating magnetic field in response to an impressed alternating current, said rotor being responsive to said alternating magnetic field for alternately accelerating in one direction and then in the opposite direction.

11. A cast cutter in accordance with claim 9, wherein said cast cutter further includes control circuitry means for varying the oscillatory rotational frequency and excursion angle under operator control.

12. A cast cutter in accordance with claim 9, wherein the outside surface of said hollow tubular member is covered by an insulation layer generally between said rotor and said front end of said hollow tubular member.

13. A cast cutter in accordance with claim 9, wherein additional mass is provided proximate said front end of said hollow tubular member, approximately three quarters of the total spring/mass system weight being adjacent said back end of said spring/mass system, and approximately one quarter of the total spring/mass system weight being adjacent said front end of said spring/mass system.

14. A cast cutter in accordance with claim 9, further including a secondary spring/mass means interconnected to said housing for minimizing vibration of said housing.

15. A cast cutter in accordance with claim 14, wherein said housing includes an inner housing and an outer housing, said inner housing enclosing said stator and rotor assembly, said secondary spring/mass means being interconnected to said back end of said inner housing.

16. A cast cutter, comprising:
(a) a housing having a front end and a back end, said housing generally defining a motor housing portion proximate said back end, a cutting blade end portion proximate said front end, and a hand grip portion intermediate of said motor housing portion and said cutting blade end portion;

(b) an electromagnetic motor being enclosed by said motor housing portion, said electromagnetic motor including a rotor assembly and a stator assembly, said rotor assembly and said stator assembly cooperating to provide oscillatory, rotational movement of said rotor assembly;

(c) torsion means, having a front end and a back end, extending longitudinally of said housing between said motor housing portion and said cutting blade end portion, a first end of said torsion means being fixedly secured against rotational movement in said motor housing portion;

(d) a hollow tubular shaft, having a front end and a back end, concentrically positioned about said torsion means and extending along a major portion thereof, said hollow tubular shaft being rotatably supported by suitable bearing means in said housing, said hollow tubular shaft being fixedly interconnected to said rotor assembly for oscillatory rotational movement therewith, said hollow tubular shaft being fixedly secured proximate said front end to proximate said front end of said torsion means to provide oscillatory rotational movement of said front end of said torsion means; and (e) said hollow tubular shaft and said torsion means interconnecting said electromagnetic motor to a cutting blade at the cutting blade end portion of the housing, said hollow tubular member being inherently more resistant to twisting movement than said torsion means, said hollow tubular shaft and said torsion means cooperating to provide a primary spring/mass system providing oscillatory rotational cutting blade motion, said primary spring/mass system having a natural frequency which is approximately that of the desired operating frequency.

17. A cast cutter in accordance with claim 16, further including a secondary spring/mass system mechanically interconnected to said housing proximate said back end, said secondary spring/mass system having a natural frequency approximately that of said primary spring/mass system, said secondary spring/mass system oscillating 180 degrees out of phase from the primary spring/mass system to minimize vibration.

* * * * *